US011723839B2

United States Patent
Wabel et al.

(10) Patent No.: US 11,723,839 B2
(45) Date of Patent: Aug. 15, 2023

(54) MAGAZINE HAVING SOLUTION BAGS FOR DIALYSIS AND METHOD FOR FILLING SAME

(71) Applicant: Fresenius Medical Care Deutschland GmbH, Bad Homburg (DE)

(72) Inventors: Peter Wabel, Rosbach (DE); Robert Berlich, St. Wendel (DE); Marcus Breuninger, Bad Homburg (DE); Birgit Staude, Pfungstadt (DE); Stefan Weiss, Bad Homburg (DE); Zdenek Cerman, Idstein (DE); Matthias Rau, Wiesbaden (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 329 days.

(21) Appl. No.: 16/971,342

(22) PCT Filed: Feb. 14, 2019

(86) PCT No.: PCT/EP2019/053667
§ 371 (c)(1),
(2) Date: Aug. 20, 2020

(87) PCT Pub. No.: WO2019/162183
PCT Pub. Date: Aug. 29, 2019

(65) Prior Publication Data
US 2021/0015706 A1    Jan. 21, 2021

(30) Foreign Application Priority Data
Feb. 21, 2018    (DE) .................. 10 2018 103950.6

(51) Int. Cl.
*A61J 1/16*        (2023.01)
*A61M 1/16*        (2006.01)
(Continued)

(52) U.S. Cl.
CPC . *A61J 1/16* (2013.01); *A61J 1/10* (2013.01); *A61J 1/1475* (2013.01);
(Continued)

(58) Field of Classification Search
CPC ..... A61J 1/16; A61J 1/1462; B05B 11/00412; B65B 1/18; B65B 3/17
(Continued)

(56) References Cited

U.S. PATENT DOCUMENTS 4,565,073 A * 1/1986 Lavender ............. A01N 1/02
                                                            220/532
5,606,934 A    2/1997 Giertych
(Continued)

FOREIGN PATENT DOCUMENTS

DE    69705816    4/2002
DE    69632709    6/2005
(Continued)

*Primary Examiner* — Timothy L Maust
(74) *Attorney, Agent, or Firm* — Jacobson Holman PLLC

(57) ABSTRACT

The present invention relates to a magazine having a plurality of solution bags for dialysis received therein, wherein the plurality of solution bags are identical; wherein the plurality of solution bags are fixed in a stationary manner in an identical orientation at different, but identically designed holding positions of the magazine; and wherein the holding positions are configured such that the solution bags can be removed from the magazine. The invention furthermore relates to a method of filling the solution bags.

10 Claims, 3 Drawing Sheets

Figure 1A:
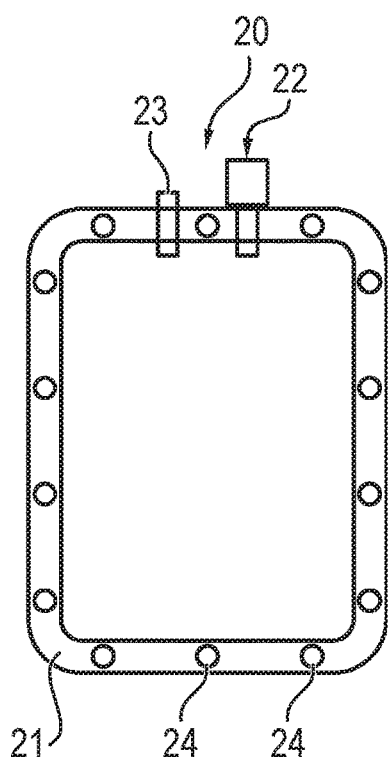
Figure 1B:
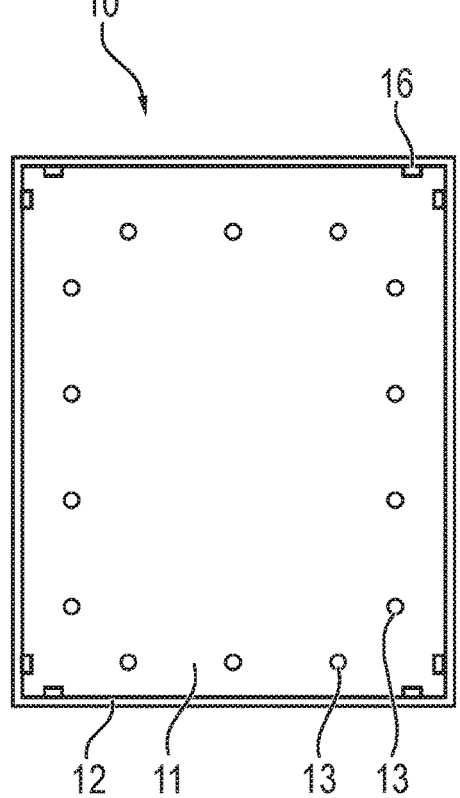
Figure 1C:
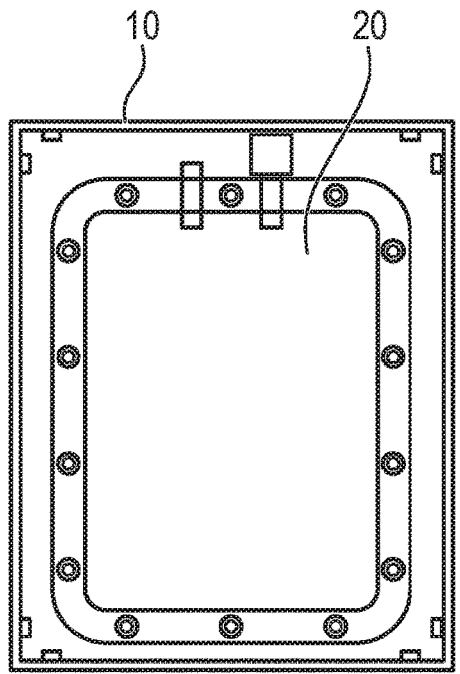
Figure 1D:
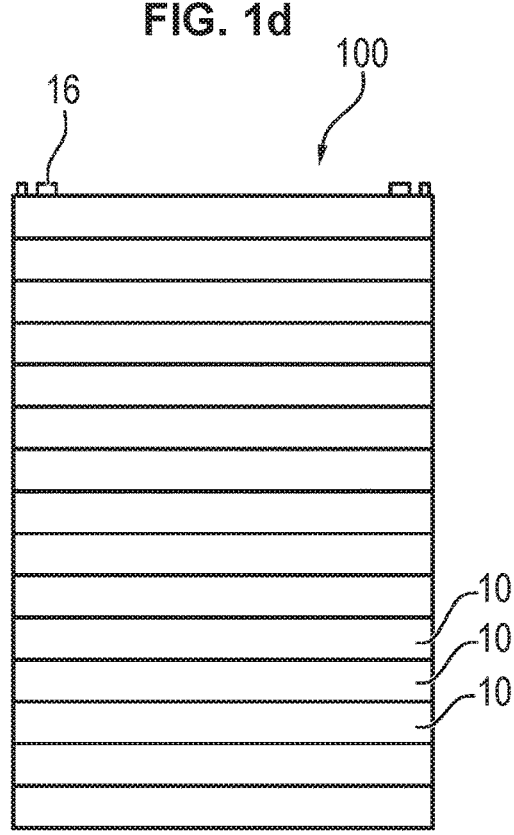

(51) Int. Cl.
  *A61J 1/10*  (2006.01)
  *A61J 1/14*  (2023.01)
  *A61M 1/28*  (2006.01)
  *B65B 3/00*  (2006.01)
  *B65B 43/14* (2006.01)

(52) U.S. Cl.
  CPC .......... *A61M 1/1668* (2014.02); *A61M 1/287* (2013.01); *A61M 2209/045* (2013.01); *B65B 3/003* (2013.01); *B65B 43/14* (2013.01)

(58) Field of Classification Search
  USPC ..................... 53/469; 141/10, 99, 114, 237
  See application file for complete search history.

(56) References Cited

U.S. PATENT DOCUMENTS

| | | | | |
|---|---|---|---|---|
| 5,614,412 | A * | 3/1997 | Smith | A61J 3/002 435/809 |
| 6,378,314 | B1 * | 4/2002 | Clark | F17C 3/10 62/51.1 |
| 6,508,800 | B1 | 1/2003 | Keilman et al. | |
| 7,104,074 | B2 * | 9/2006 | Voute | A61M 1/0277 62/62 |
| 8,151,835 | B2 * | 4/2012 | Khan | B65B 3/003 141/315 |
| 8,333,224 | B2 * | 12/2012 | Sheehy | B65B 43/54 141/10 |
| 9,346,571 | B2 * | 5/2016 | Provitera | B29C 66/73921 |
| 10,138,025 | B2 * | 11/2018 | Nakamura | B65D 33/14 |
| 10,660,821 | B2 * | 5/2020 | Tsuno | F25D 11/003 |
| 10,772,799 | B2 * | 9/2020 | Schneider | A61J 3/002 |
| 2001/0015056 | A1 | 8/2001 | Hiramoto et al. | |
| 2006/0048486 | A1 * | 3/2006 | Laing | B65D 25/107 108/51.11 |
| 2007/0209960 | A1 | 9/2007 | Leoncavallo et al. | |
| 2008/0256905 | A1 * | 10/2008 | Graf | B65B 43/262 53/384.1 |
| 2009/0009179 | A1 | 1/2009 | Sobue et al. | |
| 2019/0021948 | A1 * | 1/2019 | Ohashi | A61M 1/0209 |

FOREIGN PATENT DOCUMENTS

| | | |
|---|---|---|
| DE | 102015016749 | 6/2016 |
| DE | 102015010467 | 2/2017 |
| JP | 58109064 | 5/1991 |
| JP | 06285136 | 10/1994 |
| JP | 2008525125 | 7/2008 |
| JP | 2013514099 | 4/2013 |
| WO | WO2014/171814 | 10/2014 |
| WO | WO2017012763 | 1/2017 |

* cited by examiner

MAGAZINE HAVING SOLUTION BAGS FOR DIALYSIS AND METHOD FOR FILLING SAME

The invention relates to a magazine having solution bags for dialysis and to a method for filling same.

It is in particular customary in the field of peritoneal dialysis to provide the patient with solution bags that are filled with a dialysis solution suitable for the patient. The patient then connects these solution bags to an inflow hose independently or with the aid of trained medical personnel to fill the peritoneum with the solution.

In manufacture, prefabricated bags are filled with dialysis solution or solution concentrate and water through a filling hose or through another filling opening and the filling hose or the opening is then sealed. The manufacture and filling of the bags previously took place in the factory of the manufacturer as a rule. In the more recent past, however, concepts for a decentralized filling of the dialysis bags have been presented, with reference being able to be made by way of example to WO 2017/127632 A1 in this connection.

It is the object of the invention to propose a concept for providing and filling bags with dialysis solution that can in particular result in a simplification and in increased process security as part of a decentralized bag filling.

Against this background, the invention relates to a magazine having a plurality of solution bags for dialysis received therein, wherein the plurality of solution bags are identical; wherein the plurality of solution bags are fixed in a stationary manner in an identical orientation at different, but identically designed holding positions of the magazine; and wherein the holding positions are configured such that the solution bags can be removed from the magazine.

Such a magazine can be transported as a whole to a decentralized filling station and can be inserted as a consumable into a filling robot there. Individual solution bags can there be removed one after the other from the magazine and then filled in an automated manner. The automation of the process is made possible or facilitated by the identical design of the holding positions and by the positioning of the solution bags at the holding positions.

Provision is made in an embodiment that the solution bags are bags of connected and preferably welded plastic films. The films can be transparent to be able to visually recognize the filling. They can furthermore be designed in multiple layers to be able to achieve a high barrier effect for gases required inter alia for bicarbonate-buffered solutions.

Provision is made in an embodiment that the solution bags have a material projection which is not in direct contact with the internal volume and in which at least one hole or a zone of weakened material is preferably worked, with the material projection preferably being a peripheral weld seam.

Provision is made in an embodiment that the solution bags each have a hole or a zone of weakened material at least in their four corner regions. A larger number of holes or zones of weakened material distributed over the periphery is, however, also conceivable in an alternative variant. The holes or zones of weakened material are preferably substantially of dot form. They can serve to be able to guide a pin through the solution bag and thus to allow a stationary fixing in the magazine.

Provision is made in an embodiment that each solution bag has a filling port and/or a removal port. The ports can be implemented by lines that are enclosed between the film layers of the solution bag and can extend from the outside into the internal volume of the solution bag. The lines are preferably surrounded by a weld seam of the bag. The removal ports and filling ports of a bag can each be arranged next to one another at the same edge of the bag. Such ports can be produced particularly simply and with a small material effort and produce a flat bag design.

Provision is made in an embodiment that the magazine has a plurality of identical carriers in which one respective solution bag is fixed, with the carriers being directly stacked on one another. The stacking can take place in a horizontal direction in the sense of a stacking next to one another and in a vertical direction in the sense of a stacking above one another. A stacking in the vertical direction is preferred. The carriers can, for example, be produced from a rigid plastic material. The oppositely disposed sides of the carriers can optionally be provided with corresponding positioning aids to fix the relative position with respect to one another. Suitable positioning aids comprise corresponding webs and latch positions.

Provision is made in an embodiment that the carriers have an areal base element and a framework extending in the normal direction, wherein the solution bag lies on the base element and is surrounded by the framework. These carriers can be stacked at one another in the magazine such that the lowers sides of the base elements of the carriers lie on the frameworks of the respective preceding carriers and volumes in which the solution bags are located are thus enclosed between the base elements of adjacent carriers and the frameworks. The height of the framework can preferably be selected such that a bulge of the solution bags is only made possible to a very small degree. A uniform distribution of the concentrate over the inner volumes of the solution bags can thus be ensured in a case in which the solution bags are prefilled with a liquid concentrate.

Provision is made in an embodiment that the carriers have at least one pin, and preferably four pins, that project(s) in the normal direction from the base element, with provision preferably being made that the pins are led through material sections of the solution bag to fix it in a stationary manner. A plurality of pins can be arranged such that they are arranged distributed at regular intervals over the periphery of the solution bag and are guided in the marginal region to be able to fix it in a spread out position. In the case of four pins, they and the solution bag can be arranged such that the pins are guided through the corners of the solution bag and can thus fix it in a spread out position. Provided that the solution bags have holes or zones of weakened material, for example in a peripheral weld seam, the pins can be led through the holes or zones of weakened material. A piercing of the bag film by pointed pins is also otherwise conceivable.

Alternatively or additionally to the pins, the carriers can, for example, have clamps or suction cups to be able to fix the solution bag therein in a stationary manner and in a spread out position.

Provision is made in an embodiment that the magazine has a common frame having a plurality of slots at which the plurality of solution bags can be placed. Such an embodiment can have the advantage that the magazine comprises fewer individual parts.

Provision is made in an embodiment that the frame has a perforated plate having a plurality of elongate holes and the solution bags each have a peg, wherein the elongate holes each have a latching position, that is preferably separated by holding projections, at an end of the elongate hole and have an extended portion at the other end or are open toward the margin of the perforated plate, and wherein the pegs have a collar whose diameters are larger than the width of the elongate hole, but smaller than the diameter of the extended portion. The pegs can, for example, be formed by sections of a filling port or removal port projecting from the solution bag. The pegs of the solution bags can be inserted into the latching positions of the elongate holes, with the collar providing security against a movement normal to the perforated plate. The solution bags can thus only be removed from the latching positions in that the pegs are displaced in the plane of the perforated plate in the elongate holes and are moved, against a possible resistance on the overcoming of the holding projections, from the latching positions toward the extended portion or toward the margin of the perforated plate. This movement can be carried out in an automated manner in a filling robot. The perforated plate is preferably aligned horizontally and the solution bags preferably extend downwardly starting from the peg.

Provision is made in an embodiment that the frame is releasable fastened to a box and is preferably suspended at the upper edges of oppositely disposed side walls of the box. The frame can have a suspension apparatus at oppositely disposed sides for this purpose. If the solution bags extend downwardly starting from the frame, they can thus be received and protected within the box. The frame can, for example, be fastened to the box for transportation and can be removed from the box manually or automatically in a filling station. It can, however, also remain fastened to the box in the filling station.

Provision is made in an embodiment that the solution bags are filled with a concentrate for preparing a dialysis solution. The solution bags of the magazine can here all be filled with the same concentrate or with different concentrates. The concentrate can take up less than 40%, and preferably less than 20%, of the volume capacity of the bag. The bags prefilled in this manner required substantially less space than bags that are already filled with a finished dialysis solution.

The invention further relates to a method of filling the solution bags of the magazine in accordance with the invention, wherein the magazine is inserted into a filling robot and individual solutions bags are then removed from the magazine and then filled or are filled and then removed from the magazine as part of a preferably automated process. The filling port can be sealed after the filling. The filling of the solution bags by the filling robot can take place with water in the case of solution bags prefilled with a liquid or solid solution concentrate or otherwise with a dialysis solution.

The method can preferably be carried out in a decentralized and, optionally, mobile unit for preparing dialysis solutions on site and for the direct administration to the patient. The prefilling of the solution bags with concentrate, where present, can in this case already be carried out in the factory so that the magazine can already be transported to a decentralized filling unit in the prefilled state.

The invention further relates to a system of a filling robot and a magazine as described herein, wherein the filling robot comprises a receiver in which the magazine can be received in an exact fit. The filling robot can comprise a control unit that is configured to carry out a method in accordance with the invention. The filling robot can be arranged in a decentralized unit as described above for the preparation of dialysis solutions on site and for the direct administration to the patient.

Provision is made in an embodiment that the magazine is automatically introduced into a receiver of the filling robot so that the solution bags are present in a position suitable for removal, and optionally filling, and so that the magazine is automatically removed again from the receiver after the removal. A drawing in or a raising from a loading surface of a decentralized unit can be provided, for example. The receiver of the filling robot can be configured such that the magazine is received in an exact fit.

Further details and advantages of the invention result from the embodiments described in the following with reference to the Figures. There are shown in the Figures:

FIG. 1: an embodiment of a magazine in accordance with the invention;

FIG. 2: possible variants of the fixing of a solution bag in carriers of the magazine of FIG. 1; and FIG. 3: a further embodiment of a magazine in accordance with the invention.

An embodiment of a magazine 100 in accordance with the invention is shown in FIG. 1. The magazine 100, as shown in FIG. 1d, comprises a plurality of identical carriers 10, shown in FIG. 1c, in which one respective solution bag 20 is fixed. An individual solution bag 20 is shown in FIG. 1a; a carrier 10 with a solution bag 20 fixed therein in FIG. 1c. The carriers 10 each have a flat rectangular base plate 11 that is surrounded by a framework 12 extending upwardly in a normal direction. They are produced from a rigid plastic material.

The likewise substantially rectangular solution bags 20, whose dimensions are, however, smaller than the dimensions of the base plates 11, lie on the base plates 11. They are surrounded by the framework 12, but do not contact it. The solution bags 20 are formed by a peripheral welding of two plastic films and correspondingly have a peripheral weld seam 21. The plastic films are designed in multiple layers and are transparent. The solution bags 20 each have a filling port 22 and a removal port 23. The ports 22 and 23 are implemented by lines which extend from the outside into the inner volume of the solution bag 20, which are surrounded by a weld seam 21 of the bag 20, and which are thus enclosed between the film layers of the solution bag 20. The ports 22 and 23 are arranged next to one another at the same edge of the bag 20.

To be able to fix the bags 20 in a stationary manner and in a spread out position on the base plates 11, holes 24 are worked into the weld seam 21 of the bags 20 at regular intervals over the periphery of the bag. The base plates 11 have pins at corresponding positions that project upwardly in the normal direction and that are led through the holes 24 of the solution bag 20.

Figure 2A:
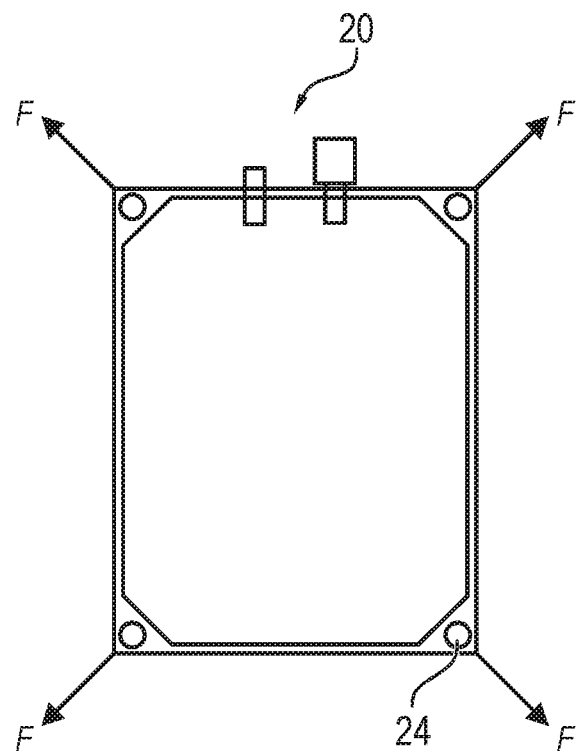
Figure 2B:
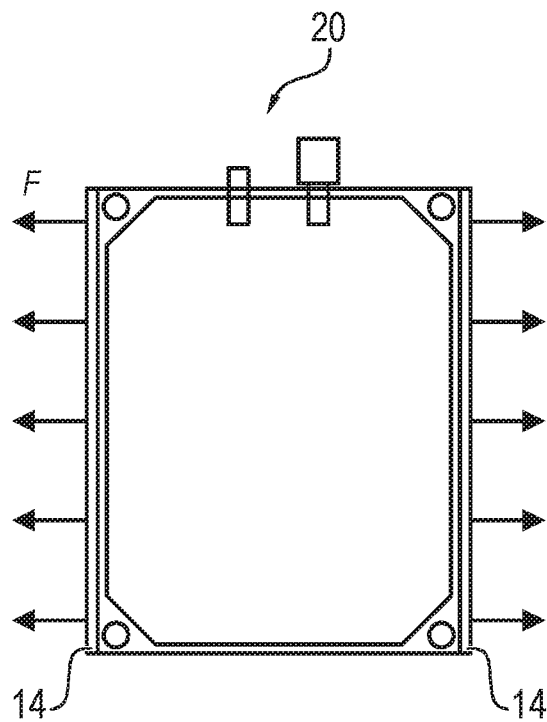
Figure 2C:
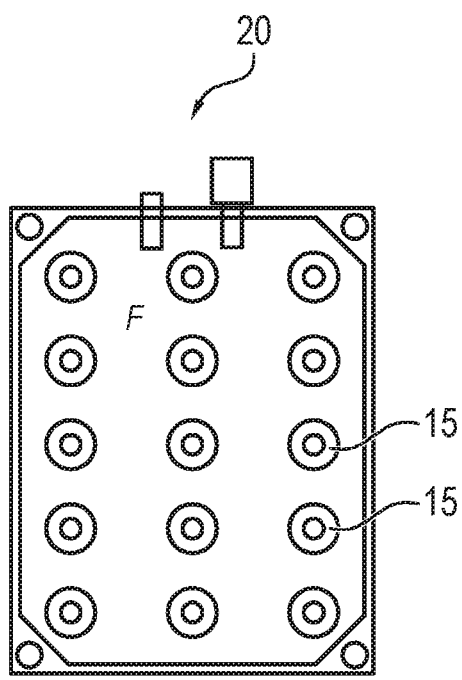

Alternative variants of a fixing of the bags 20 on the base plates 11 are shown in FIG. 2. In a variant in accordance with FIG. 2a, only four holes 24 are present at the four corner points of the bag 20 and corresponding pins 13 of the carriers 10 are led through them. As indicated by arrows in FIG. 2a, the fixing at these four points is sufficient to fix the bag 20 in an extended position. In a further variant in accordance with FIG. 2b, the bag 20 is held in each case over the total length at two oppositely disposed sides in that the weld seam 21 is fixed in a clamp 14. In yet another variant in accordance with FIG. 2c, suction cups 15 are arranged distributed over the base plate 11 to fix the bag 20.

The carriers 10 are stacked directly above one another in a vertical direction to form the magazine 100. The upper sides and the lower sides of the carriers 10 are provided with corresponding webs 16 and latch positions at the four corners to fix the relative positions of the stacked carriers 10 with respect to one another.

Volumes in which the solution bags 20 are located are enclosed by the base plates 11 of adjacent carriers 10 and by the frameworks 12 of the carriers 10 due to the stacking. The height of the framework 12 is selected such that a bulge of the solution bags 20 is only made possible to a very small degree. A uniform distribution of the concentrate over the inner volumes of the solution bags 20 can thus be ensured in a case in which the solution bags 20 are prefilled with a liquid concentrate. The fixing of the solution bags 20 in their stretched positions, by the measure shown in FIG. 1 or alternatively by the measures shown in FIG. 2, likewise ensures a uniform distribution of the concentrate, where present, over the inner volumes of the solution bags 20.

The magazine 100 can be transported as a whole to a decentralized filling station and can be inserted as a consumable into a filling robot there. Individual carriers can there be taken from the magazine 100 one after the other in an automated manner and the solution bags 20 can then be removed from the carrier 10 and filled. The automation of the process is simplified by the identical design of the carriers 10 and by the identical positioning of the solution bags 20 in the carriers 10.

FIG. 3 shows a further embodiment of a magazine 100 in accordance with the invention. In this embodiment, the magazine 100 comprises a common frame 30 having a plurality of solution bags 20 placed on.

Figure 3A:
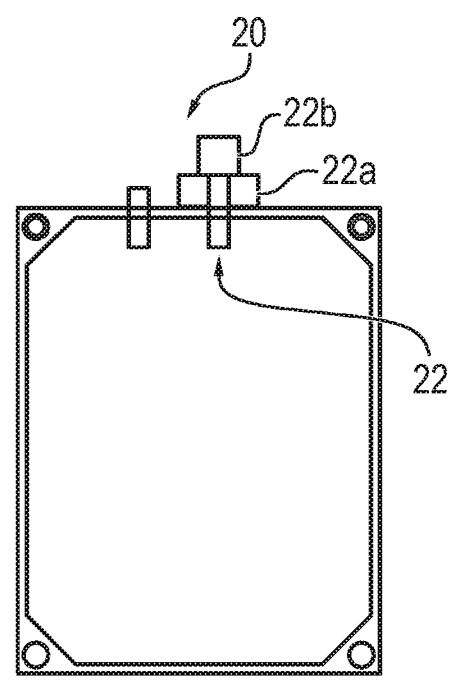

The solution bags 20 are, as can be seen in FIG. 3*a*, of a substantially identical design to the solution bags 20 shown in FIG. 2*a*, with the only difference that the filling port 22 is somewhat extended toward the outside and comprises a neck section 22*a* as well as a collar 22*b* widened with respect thereto.

Figure 3B:
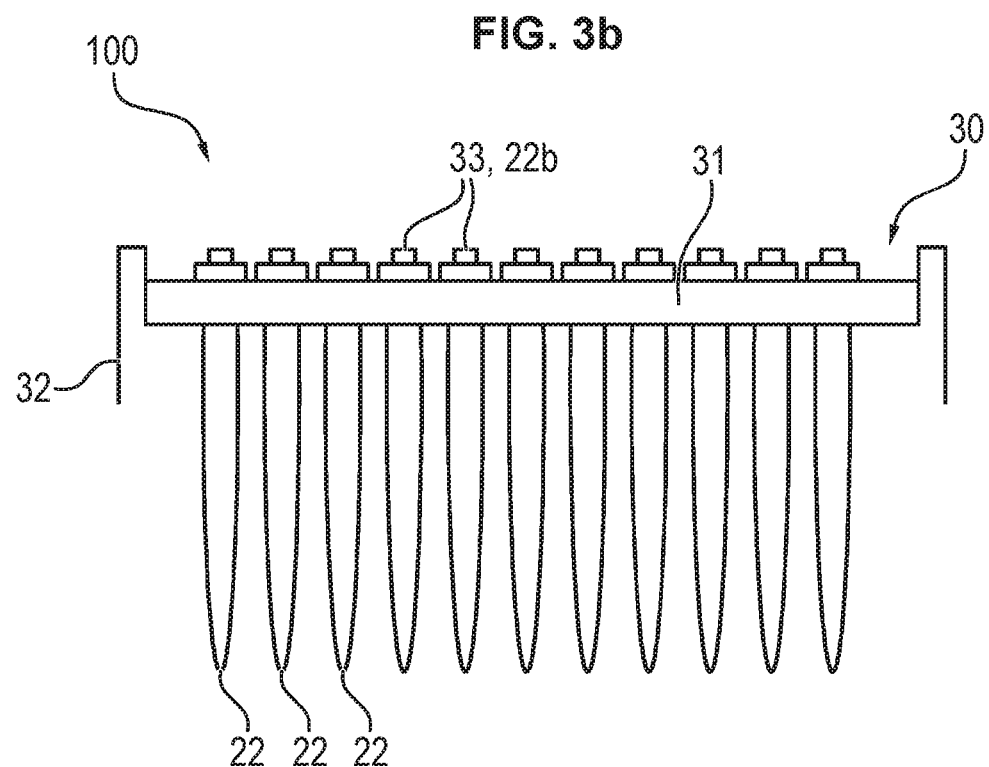

The frame 30 comprises an elongate perforated plate 31 as well as suspension lugs 32 fastened to oppositely disposed front sides of the perforated plate 31, as can be recognized in FIG. 3*b*. The perforated plate 31 comprises a plurality of slots 33 for the solution bags 20 at which their filling ports 22 are placed.

Figure 3C:
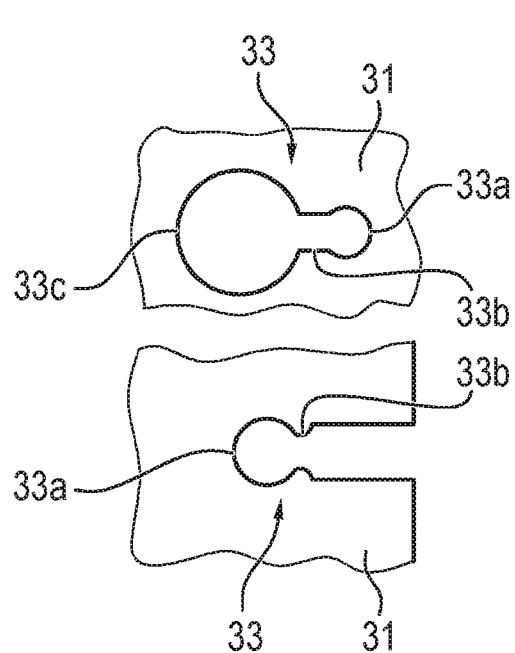

The slots 33 can be configured such as shown in the plan views of FIG. 3*c*. The slots 33 are namely elongate holes that have a latching position 33*a* at one end that is delineated by holding projections 33*b* with respect to the other zones of the elongate hole. It is either extended (upper image of FIG. 3*c*) at the oppositely disposed end of the elongate hole or is open toward the margin of the perforated plate 31 (lower image of FIG. 3*c*). The filling ports 22 of the solution bags 20 are inserted into these slots 33 such that the neck 22*a* passes through the elongate hole at the latching position 33*a* and the collar 22*b* secures the filling ports 22 against a release normal to the perforated plate 31. The solution bag 20 can thus only be removed from the slots 33 in that the filling port 22 is displaced in the elongate holes in the plane of the perforated plate 31 and is moved against a resistance on the overcoming of the holding projections 33*b* from the latching positions 33*a* toward the extended portion 33*c* (upper image of FIG. 3*c*) or toward the margin of the perforated plate 31 (lower image of FIG. 3*c*). This movement can be carried out in an automated manner in a filling robot.

The perforated plate 31 is aligned horizontally and the solution bags 20 extend downwardly in the suspended state starting from the filling port 22. The slots 33 are staggered in a row in the longitudinal direction of the perforated plate 31, which applies correspondingly to the inserted solution bags 20.

Figure 3D:
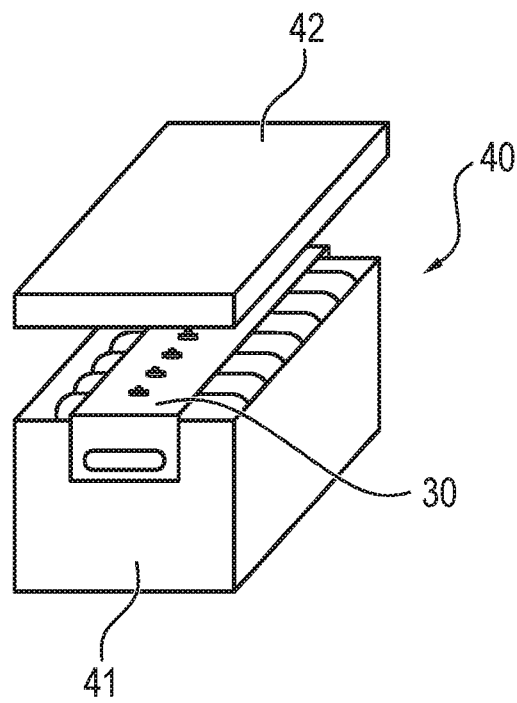

As can be seen from FIG. 3*d*, the suspension lugs 32 of the frame 30 are suspended at the upper edges of oppositely disposed side walls 41 of a box 40. The bags 20 hanging downwardly from the perforated plate 31 are thus received and protected in the inner space of the box 40. The filled box 40 can be additionally covered by a cover 42 for transportation.

Also like the magazine 100 of FIG. 1, the magazine 100 of FIG. 3 can also be transported as a whole to a decentralized filling station and can be inserted as consumer material into a filling robot there. During transport, the frame 30 can be fastened to the box 40 and can be removed from the box 40 manually or automatically in a filling station and can be inserted at a storage position at the filling robot. Individual solution bags 20 can there be taken from the frame 33 one by one in an automated manner and can then be filled. The automation of the process is simplified by the identical design of all the slots 33 and by the identical positioning of the solution bags 20 in the slots 33.

The solution bags can already be prefilled with concentrate, for example in the factory, before their transportation to the decentralized filling station and their insertion there into a filling robot so that they only have to be filled up in the decentralized filling station with deionized water that can optionally still have variable components of the dialysis solution that are not taken into account in the concentrate.

The invention claimed is:

1. A magazine having a plurality of solution bags for dialysis received therein, wherein the plurality of solution bags are identical; wherein the plurality of solution bags are fixed in a stationary manner in an identical orientation at different, but identically designed holding positions of the magazine; and wherein the holding positions are configured such that the solution bags can be removed from the magazine, characterized in that the magazine has a plurality of identical carriers in which a respective one solution bag is fixed, with the carriers being stacked directly at one another, characterized in that the carriers have an areal base element and a framework extending in the normal direction, wherein the solution bag lies on the base element and is surrounded by the framework, and characterized in that the carriers have at least one pin that projects in the normal direction from the base element, with provision being made that the at least one pin is led through material sections of the solution bag to fix it in a stationary manner.

2. A magazine in accordance with claim 1, characterized in that the solution bags are bags composed of connected and advantageously welded plastic films.

3. A magazine in accordance with claim 1, characterized in that the solution bags have a material projection which is not in direct contact with the internal volume and in which at least one hole or a zone of weakened material is preferably worked, with the material projection preferably being a peripheral weld seam.

4. A magazine in accordance with claim 1, characterized in that the solution bags are filled with a concentrate for preparing a dialysis solution.

5. A magazine in accordance with claim 4, characterized in that the concentrate takes up less than 40% of the volume capacity of the bag.

6. A method of filling the solution bags of a magazine in accordance with claim 1, wherein the magazine is inserted into a filling robot and individual solutions bags are then removed from the magazine and then filled or are filled and then removed from the magazine as part of an automated process.

7. A method in accordance with claim 6, characterized in that the magazine is automatically introduced into a receiver of the filling robot so that the solution bags are present in a position suitable for the removal and, optionally, filling and so that the magazine is automatically removed from the receiver again after the removal.

8. A system comprising a magazine in accordance with claim 1 and a filling robot, wherein the filling robot comprises a receiver in which the magazine can be received in an exact fit.

9. A magazine having a plurality of solution bags for dialysis received therein, wherein the plurality of solution bags are identical; wherein the plurality of solution bags are fixed in a stationary manner in an identical orientation at different, but identically designed holding positions of the magazine; and wherein the holding positions are configured such that the solution bags can be removed from the magazine, characterized in that the magazine has a common frame having a plurality of slots at which the plurality of solution bags are placed, and characterized in that the frame has a perforated plate having a plurality of elongate holes and the solution bags each have a peg, wherein the elongate holes each have a slot, that is separated by holding projections, at an end of the elongate hole and have an extended portion at the other end or are open toward the margin of the perforated plate, and wherein the pegs have a collar whose diameters are larger than the width of the elongate hole, but smaller than the diameter of the extended portion.

10. A magazine in accordance with claim 9, characterized in that the frame is releasably fastened to a box and is suspended at the upper edges of oppositely disposed side walls of the box.

\* \* \* \* \*